(12) United States Patent
Rodeheaver et al.

(10) Patent No.: US 12,403,002 B2
(45) Date of Patent: Sep. 2, 2025

(54) HYBRID POWER DELIVERY FOR SURGICAL IMPLANTS

(71) Applicant: Alcon Inc., Fribourg (CH)

(72) Inventors: Austin Xavier Rodeheaver, Arlington, TX (US); Todd Taber, Keller, TX (US); Roderick Van Den Bergh, Cambridge (GB); Marshall Keith Proulx, Keller, TX (US); Grant Corthorn, Cambridge (GB); Christopher Hemmingway, Cambridge (GB); Martin Orrell, Cambridge (GB); Catherine Wyman, Cambridge (GB); Trevor Penhallurick, Cambridge (GB)

(*) Notice: Subject to any disclaimer, the term of this patent is extended or adjusted under 35 U.S.C. 154(b) by 9 days.

(21) Appl. No.: 17/645,372

(22) Filed: Dec. 21, 2021

(65) Prior Publication Data
US 2022/0192819 A1    Jun. 23, 2022

Related U.S. Application Data

(60) Provisional application No. 63/129,026, filed on Dec. 22, 2020.

(51) Int. Cl.
*A61F 2/16*    (2006.01)

(52) U.S. Cl.
CPC .......... *A61F 2/167* (2013.01); *A61F 2/1675* (2013.01); *A61F 2/1678* (2013.01);
(Continued)

(58) Field of Classification Search
CPC ...... A61F 2/167; A61F 2/1675; A61F 2/1678; A61F 2230/0093; A61F 2250/0003; A61F 2250/0069; A61F 2/1672
See application file for complete search history.

(56) References Cited

U.S. PATENT DOCUMENTS

| 4,335,191 A | 6/1982 | Peled |
| 5,506,068 A | 4/1996 | Dan et al. |

(Continued)

FOREIGN PATENT DOCUMENTS

| EP | 1800623 A1 | 6/2007 |
| EP | 1857076 B1 | 7/2010 |

(Continued)

OTHER PUBLICATIONS

PulsesPlus™ Series—Bobbin-Type LiSOCl2 Batteries with Hybrid Layer Capacitors. Datasheet [online] Tadiran Batteries [retrieved on Apr. 17, 2025]. Retrieved from the Internet:.

*Primary Examiner* — Tan-Uyen T Ho
*Assistant Examiner* — Chima U Igboko

(57) ABSTRACT

A hybrid power system for delivering an implant to an eye using hydraulic fluid flow or pressure. An implant may be stored, advanced, and delivered to an eye using hydraulic fluid stored in a sterile container through a hollow advancement plunger. The plunger may rigidly advance the implant to a sealed position in a first phase, and then the implant may be advanced into the eye via hydraulic pressure or fluid flow in a second phase. The power system may provide a first cell having a first power density and a second cell having a second power density, wherein the second power density is greater than the first power density. A controller may use the first cell during the first delivery phase and the second cell during the second delivery phase.

13 Claims, 6 Drawing Sheets

(52) U.S. Cl.
CPC ............... *A61F 2230/0093* (2013.01); *A61F 2250/0003* (2013.01); *A61F 2250/0069* (2013.01)

(56) References Cited

U.S. PATENT DOCUMENTS

| | | | |
|---|---|---|---|
| 5,998,052 | A | 12/1999 | Yamin |
| 7,156,854 | B2 | 1/2007 | Brown et al. |
| 8,308,736 | B2 | 11/2012 | Boukhny et al. |
| 8,308,799 | B2 | 11/2012 | Chen et al. |
| 8,313,860 | B2 | 11/2012 | Yamin et al. |
| 8,377,076 | B2 | 2/2013 | Downer et al. |
| 8,956,408 | B2 | 2/2015 | Smiley et al. |
| 8,968,396 | B2 | 3/2015 | Matthews et al. |
| 9,480,555 | B2 | 11/2016 | Downer et al. |
| 9,610,155 | B2 | 4/2017 | Matthews et al. |
| 9,693,858 | B2 | 7/2017 | Hildebrand et al. |
| 9,855,139 | B2 | 1/2018 | Matthews et al. |
| 10,172,706 | B2 | 1/2019 | Auld et al. |
| 10,195,020 | B2 | 2/2019 | Matthews et al. |
| 10,568,735 | B2 | 2/2020 | Brown et al. |
| 10,588,780 | B2 | 3/2020 | Van Noy et al. |
| 10,770,715 | B2 | 9/2020 | Yamin |
| 11,039,953 | B2 | 6/2021 | Balachandran |
| 11,217,787 | B2 | 1/2022 | Yamin et al. |
| 12,004,944 | B2 | 6/2024 | Weston |
| 2008/0097460 | A1 | 4/2008 | Boukhny et al. |
| 2008/0147081 | A1 | 6/2008 | Pynson |
| 2008/0221584 | A1 | 9/2008 | Downer |
| 2010/0057093 | A1 | 3/2010 | Ide et al. |
| 2011/0265779 | A1* | 11/2011 | Vandrak ............... F24H 9/06 126/93 |
| 2012/0022548 | A1 | 1/2012 | Zacharias |
| 2013/0197532 | A1 | 8/2013 | Boukhny et al. |
| 2013/0253527 | A1 | 9/2013 | Schneider et al. |
| 2014/0012277 | A1 | 1/2014 | Matthews et al. |
| 2014/0257315 | A1 | 9/2014 | Wu |
| 2014/0276898 | A1 | 9/2014 | Novak et al. |
| 2015/0238687 | A1 | 8/2015 | Novakovic et al. |
| 2015/0282928 | A1 | 10/2015 | Auld et al. |
| 2016/0087460 | A1* | 3/2016 | Rich ................... H01M 10/44 307/18 |
| 2017/0007237 | A1* | 1/2017 | Yates ............ A61B 17/320016 |
| 2017/0027686 | A1 | 2/2017 | Nagasaka |
| 2017/0119522 | A1 | 5/2017 | Auld et al. |
| 2018/0049866 | A1 | 2/2018 | Fayyaz et al. |
| 2018/0200046 | A1 | 7/2018 | Brown et al. |
| 2020/0179101 | A1 | 6/2020 | Flowers et al. |
| 2020/0179102 | A1 | 6/2020 | Chen et al. |
| 2020/0179103 | A1 | 6/2020 | Auld et al. |
| 2020/0188089 | A1 | 6/2020 | Auld et al. |
| 2020/0197170 | A1 | 6/2020 | Auld et al. |
| 2021/0052371 | A1 | 2/2021 | Singh et al. |
| 2021/0234149 | A1 | 7/2021 | Yamin et al. |
| 2022/0265420 | A1 | 8/2022 | Kelp |

FOREIGN PATENT DOCUMENTS

| | | |
|---|---|---|
| EP | 3560457 A1 | 10/2019 |
| JP | 2010063777 B | 10/2013 |
| WO | 2014145562 A1 | 9/2014 |
| WO | 2020065516 A1 | 4/2020 |
| WO | 2020128762 A1 | 6/2020 |
| WO | 2020151908 A1 | 7/2020 |

* cited by examiner

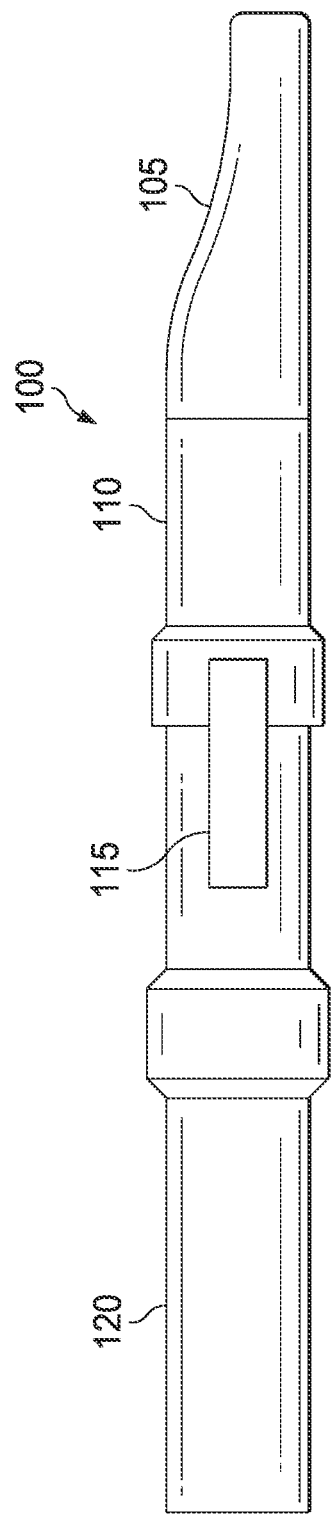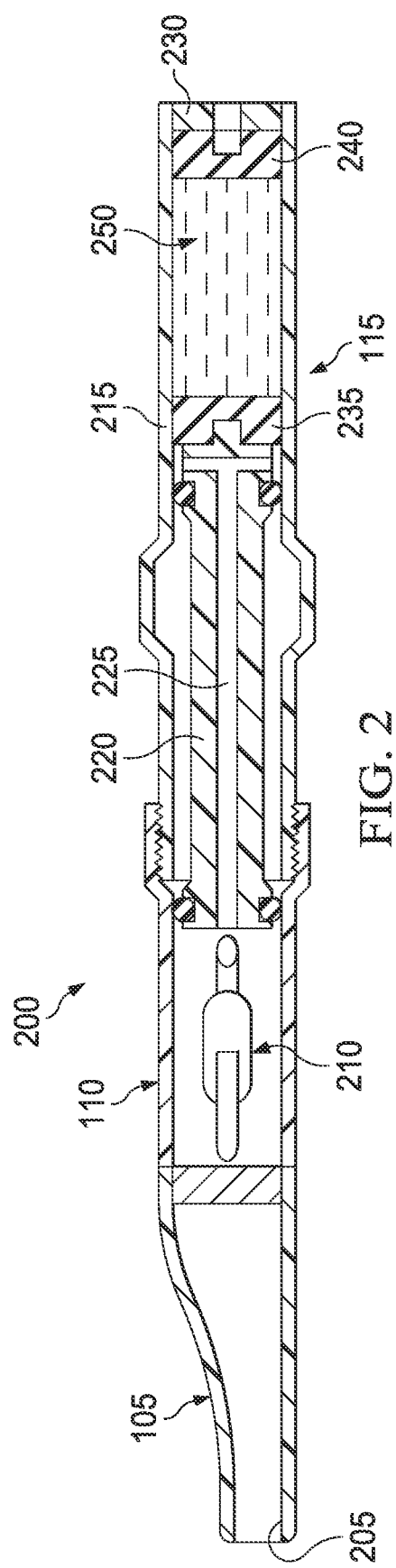

HYBRID POWER DELIVERY FOR SURGICAL IMPLANTS

PRIORITY CLAIM

This application claims the benefit of priority of U.S. Provisional Patent Application Ser. No. 63/129,026 titled "HYBRID POWER DELIVERY FOR SURGICAL IMPLANTS," filed on Dec. 22, 2020, whose inventors are Austin Xavier Rodeheaver, Todd Taber, Roderick Van Der Bergh, Marshall Keith Proulx, Grant Corthorn, Chris Hemmingway and Martin Orrell, which is hereby incorporated by reference in its entirety as though fully and completely set forth herein.

TECHNICAL FIELD

The invention set forth in the appended claims relates generally to eye surgery. More particularly, but without limitation, the claimed subject matter relates to systems, apparatuses, and methods for inserting an implant into an eye.

BACKGROUND

The human eye can suffer a number of maladies causing mild deterioration to complete loss of vision. While contact lenses and eyeglasses can compensate for some ailments, ophthalmic surgery may be required for others. In some instances, implants may be beneficial or desirable. For example, an intraocular lens may replace a clouded natural lens within an eye to improve vision.

While the benefits of intraocular lenses and other implants are known, improvements to delivery systems, components, and processes continue to improve outcomes and benefit patients.

BRIEF SUMMARY

New and useful systems, apparatuses, and methods for eye surgery are set forth in the appended claims. Illustrative embodiments are also provided to enable a person skilled in the art to make and use the claimed subject matter.

For example, some embodiments may comprise or consist essentially of an apparatus for delivering an implant, such as an intraocular lens. In more particular examples, the apparatus may comprise a rigid plunger for advancing an implant. Some embodiments may additionally comprise a bore through the rigid plunger, which can allow a working fluid to advance the implant into the eye via hydraulic pressure. For example, a hollow rigid plunger can be used to first advance an intraocular lens to a point that a seal is created about the intraocular lens within a delivery lumen. The lens may then be hydraulically advanced to delivery by passing a working fluid through the hollow bore of the plunger.

Some embodiments may comprise or consist essentially of a hybrid power module having a primary cell and a secondary cell. In some embodiments, for example, the primary cell and the secondary cell may be a primary battery and a secondary battery, wherein the primary battery and the secondary battery have different power densities. In other examples, the primary cell may be a battery and the secondary cell may be a capacitor. Each cell can provide distinct power delivery capabilities at different times during the delivery procedure. For example, the primary cell may provide a relatively lower power for initial movement of an implant over a relatively longer range in the first phase, and the secondary cell may provide a relatively higher peak power for delivery of the implant through the delivery lumen in the second phase.

More generally, some embodiments may comprise or consist essentially of an apparatus for operating an implant delivery device. Such embodiments may comprise a motor, a primary cell, a secondary cell, and a controller. The motor may be configured to be coupled to the implant delivery device. The primary cell may have a first energy density and a first power density; and the secondary cell may have a second energy density and a second power density. The controller may be coupled to the motor, the primary cell, and the secondary cell. The controller may be configured to selectively couple the primary cell to the motor for a first delivery range, couple the secondary cell to the motor for a second delivery range, and couple the primary cell to the secondary cell for a charging period. In more particular embodiments, the second power density may be greater than the first power density.

Some embodiments of an apparatus for delivering an implant to an eye may comprise a nozzle having a delivery lumen, an implant bay coupled to the nozzle, an actuator, a motor configured to be coupled to the actuator, a primary cell, and a secondary cell. A controller may be coupled to the motor, the primary cell, and the secondary cell. The controller may be configured to selectively couple the primary cell and the secondary cell to the motor. In some embodiments, the controller may couple the primary cell to the motor to operate the actuator to drive the implant from a first position to a second position and may couple the secondary cell to the motor to operate the actuator to drive the implant to a third position. In more particular embodiments, the actuator may comprise a push rod configured to engage the implant. For example, the push rod may be a rigid plunger in some embodiments. Additionally, some embodiments of the actuator may comprise a bore through the push rod, which can be fluidly coupled to the delivery lumen in the nozzle. For example, the push rod may be a hollow, rigid plunger in some embodiments. The implant may be a lens in some embodiments.

A method for delivering or ejecting an implant from a delivery system may comprise providing the implant in an implant bay, applying a first delivery force to advance the implant from the implant bay to a delivery lumen with a rigid push rod, and applying a second delivery force to advance the implant through the delivery lumen. The second delivery force may be greater than the first delivery force. In some embodiments, the push rod may comprise or consist essentially of a rigid plunger. In yet more particular embodiments, the method may additionally comprise moving a working fluid through a bore in the rigid plunger with the second delivery force.

Features, elements, and aspects described in the context of some embodiments may also be omitted, combined, or replaced by alternative features. Other features, objectives, advantages, and a preferred mode of making and using the claimed subject matter are described in greater detail below with reference to the accompanying drawings of illustrative embodiments.

BRIEF DESCRIPTION OF THE DRAWINGS

The accompanying drawings illustrate some objectives, advantages, and a preferred mode of making and using some embodiments of the claimed subject matter. Like reference numbers represent like parts in the examples.

FIG. 1 is a schematic view of an example system for inserting an implant into an eye.

FIG. 2 is a schematic diagram of an example of a delivery module that may be associated with some embodiments of the system of FIG. 1.

DESCRIPTION OF EXAMPLE EMBODIMENTS

Figure 3:
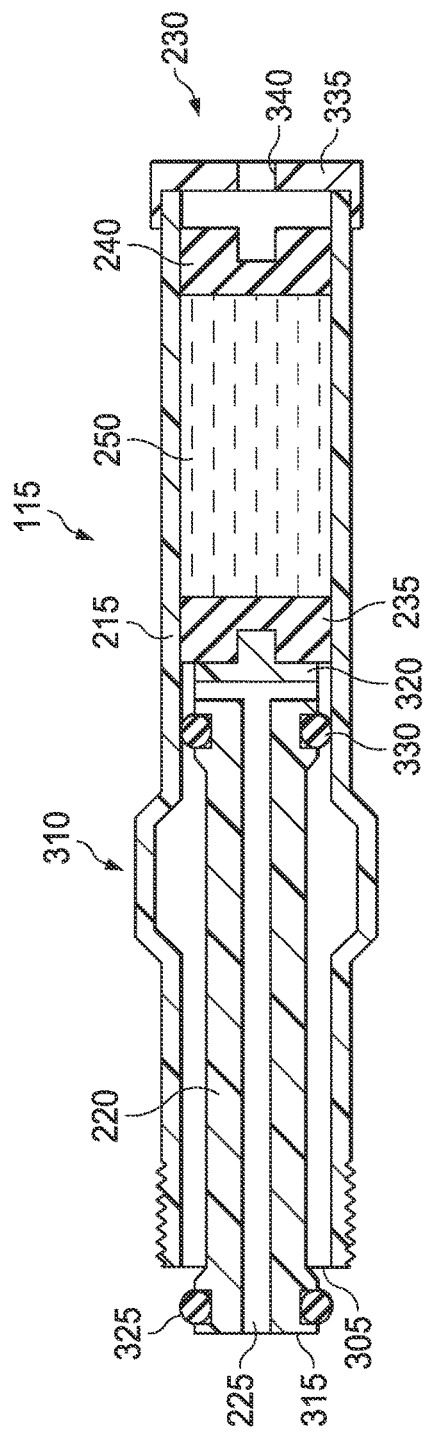
FIG. 3 is a detail view of an actuator that may be associated with the example of FIG. 2.

The following description of example embodiments provides information that enables a person skilled in the art to make and use the subject matter set forth in the appended claims, but it may omit certain details already well known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive an implant. However, as should be recognized by those skilled in the art, this frame of reference is merely a descriptive expedient rather than a strict prescription.

FIG. 1 is a schematic diagram of a system 100 that can insert an implant into an eye. In some embodiments, the system 100 may comprise two or more modules, which can be configured to be coupled and decoupled as appropriate for storage, assembly, use, and disposal. For example, as illustrated in FIG. 1, some embodiments of the system 100 may include a nozzle 105, an implant bay 110 coupled to the nozzle 105, and an actuator 115 coupled to the implant bay 110. In some embodiments, the system 100 may additionally comprise a drive module 120 configured to engage the actuator 115.

The nozzle 105 generally comprises a tip adapted for insertion through an incision into an eye. The size of the tip may be adapted to surgical requirements and techniques as needed. For example, small incisions are generally preferable to reduce or minimize healing times. Incisions of less than 3 millimeters may be preferable in some instances, and the tip of the nozzle 105 may have a width of less than 3 millimeters in some embodiments.

The implant bay 110 generally represents a wide variety of apparatuses that are suitable for storing an implant prior to delivery into an eye. In some embodiments, the implant bay 110 may additionally or alternatively be configured to prepare an implant for delivery. For example, some embodiments of the implant bay 110 may be configured to be actuated by a surgeon or other operator to prepare an implant for delivery by subsequent action of the actuator 115. In some instances, the implant bay 110 may be configured to actively deform, elongate, extend, or otherwise manipulate features of the implant before the implant is advanced into the nozzle 105. For example, the implant bay 110 may be configured to extend or splay one or more features, such as haptics, of an intraocular lens.

The actuator 115 is generally configured to advance an implant from the implant bay 110 into the nozzle 105, and thereafter from the nozzle 105 through an incision and into an eye.

The drive module 120 is generally operable to energize the actuator 115. In some examples, the drive module 120 may be operated by electrical, mechanical, hydraulic, or pneumatic power, or combinations thereof, or in some other manner. In some instances, the drive module 120 may be operated manually. According to other implementations, the drive module 120 may be an automated system.

In general, components of the system 100 may be coupled directly or indirectly. For example, the nozzle 105 may be directly coupled to the implant bay 110 and may be indirectly coupled to the actuator 115 through the implant bay 110. Coupling may include fluid, mechanical, thermal, electrical, or chemical coupling (such as a chemical bond), or some combination of coupling in some contexts. For example, the actuator 115 may be mechanically coupled to the drive module 120 and may be mechanically and fluidly coupled to the nozzle 105. In some embodiments, components may also be coupled by virtue of physical proximity, being integral to a single structure, or being formed from the same piece of material.

FIG. 2 is a schematic diagram of an example of a delivery module 200 that may be associated with some embodiments of the system 100. In the example of FIG. 2, delivery module 200 comprises the nozzle 105, the implant bay 110, and the actuator 115. The nozzle 105 of FIG. 2 has a delivery lumen 205, and an implant 210 is disposed within the implant bay 110.

The actuator 115 of FIG. 2 generally comprises a housing 215 and a push rod, such as a plunger 220, disposed within the housing 215. In some embodiments, the plunger 220 or other push rod may be comprised of a substantially rigid material, such as a medical grade polymer material. In the example of FIG. 2, the actuator 115 further comprises a bore 225 through the plunger 220 and a driver interface 230. A plunger seal 235 may be disposed within the housing 215 and coupled to the plunger 220. A drive seal 240 may also be disposed within the housing 215.

As illustrated in the example of FIG. 2, the drive seal 240 may be disposed between the plunger seal 235 and the drive interface 230, and a fluid chamber 250 may be defined within the housing 215 between the plunger seal 235 and the drive seal 240. In the example configuration of FIG. 2, the plunger seal 235 is configured to provide a fluid seal across the housing 215 and substantially prevent movement of fluid from the fluid chamber 250 to the bore 225. The drive seal 240 may also be configured to provide a fluid seal across the housing 215 and substantially prevent movement of fluid from the fluid chamber 250 to the drive interface 230.

FIG. 3 is a detail view of the actuator 115 of FIG. 2, illustrating additional details that may be associated with some embodiments. For example, the housing 215 of FIG. 3 further comprises a plunger interface 305 and a bypass channel 310 disposed between the plunger interface 305 and the drive interface 230. The bypass channel 310 may take various forms. For example, the bypass channel 310 may comprise a protrusion in the housing 215, as illustrated in FIG. 3. In other examples, the bypass channel 310 may comprise a groove or recess in the inner surface of the housing 215. In some embodiments, the bypass channel 310 may comprise a plurality of channels. For example, a plurality of channels may be disposed circumferentially around the housing 215 in some embodiments.

The plunger 220 generally has a first end 315 and a second end 320, wherein the first end 315 is generally disposed adjacent to the plunger interface 305. The bore 225 generally passes through the plunger 220 longitudinally from the first end 315 to the second end 320.

In some embodiments, the actuator 115 may additionally comprise a nozzle seal 325 and a bypass seal 330. Each of the nozzle seal 325 and the bypass seal 330 are generally configured to create a seal between a portion of the plunger 220 and the housing 215 to substantially prevent movement of fluid past the seal. As illustrated in the example of FIG. 3, one or both of the nozzle seal 325 and the bypass seal 330 may be ring seals, such as an O-ring, disposed circumferentially around a portion of the plunger 220. In other examples, an umbrella seal may be suitable. In more particular embodiments, the nozzle seal 325 may be disposed proximate to the first end 315 of the plunger 220, and the bypass seal 330 may be disposed proximate to the second end 320 of the plunger 220.

The drive interface 230 of FIG. 3 comprises a cap 335 and an aperture 340. The cap 335 may be coupled to an end of the housing 215 to retain the drive seal 240 and other components within the housing 215.

Figure 4:
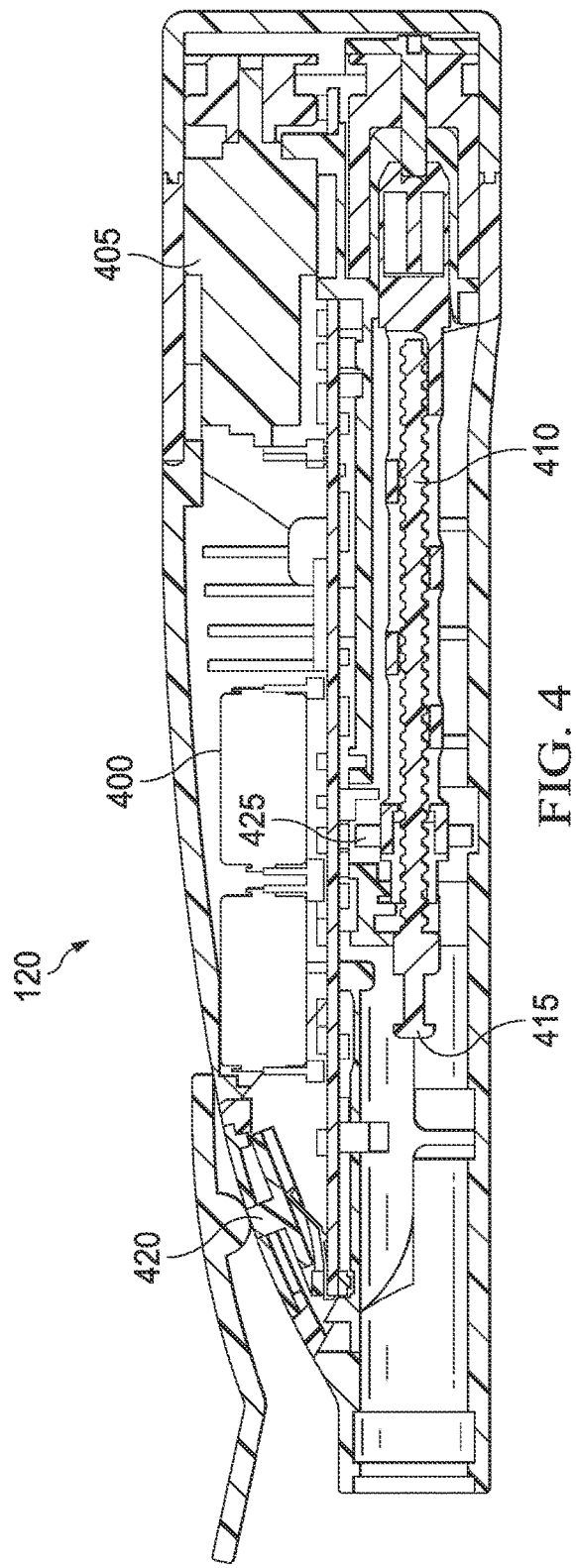
FIG. 4 is a schematic diagram of an example of a drive module that may be associated with some embodiments of the system of FIG. 1.

FIG. 4 is a schematic diagram of an example of the drive module 120 of FIG. 1, illustrating additional details that may be associated with some embodiments. For example, the drive module 120 of FIG. 4 generally comprises a power module 400 and a motor 405 coupled to the power module 400. A drive shaft 410 may be coupled to the motor 405. In some embodiments, the drive shaft 410 may comprise or consist essentially of a lead screw. In some embodiments, the drive shaft 410 may be coupled to an actuator interface 415. The drive module 120 may also comprise a switch 420 for variably controlling the speed of the motor 405, and an encoder wheel 425 for measuring movement of the drive shaft 410.

Figure 5:
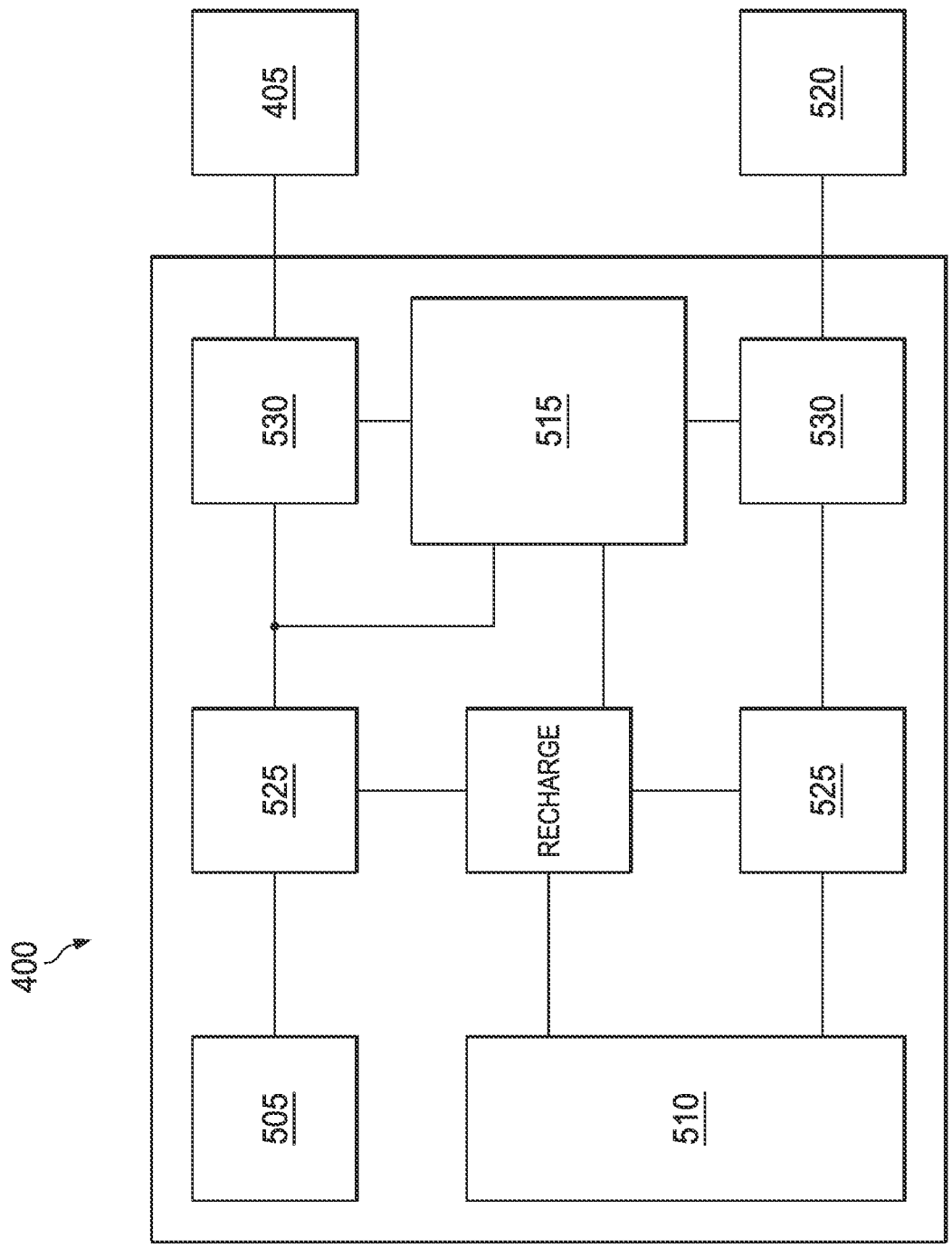
FIG. 5 is a schematic diagram of an example power module that may be associated with the drive module of FIG. 4.

FIG. 5 is a schematic diagram illustrating an example of the power module 400 that may be associated with some examples of the drive module 120. In the example of FIG. 5, the power module 400 generally comprises a primary cell 505, a secondary cell 510, and a controller 515 coupled to the primary cell 505 and the secondary cell 510. The primary cell 505 of FIG. 5 may have a first energy density and a first power density, and the secondary cell 510 may have a second energy density and a second power density. In some embodiments, the first energy density may be greater than the second energy density, and the second power density may be greater than the first power density. For example, the primary cell 505 may be a battery, which can provide a relatively higher energy density and lower power density, and the secondary cell 510 may be a capacitor, which can provide a relatively higher power density and lower energy density. In some examples, the primary cell 505 may be a lithium-based battery, and the secondary cell 510 may be a supercapacitor. As illustrated in FIG. 5, some embodiments may additionally comprise a user interface 520, one or more power conditioning units 525, and one or more electronic switching devices, such as solid-state relays 530.

The controller 515 may be configured to selectively couple the primary cell 505 to the motor 405 for a first delivery range and couple the secondary cell 510 to the motor 405 for a second delivery range. For example, in some embodiments, the controller 515 may control the solid-state relays 530 to couple and disconnect the motor 405 to the primary cell 505 and the secondary cell 510. In some embodiments, the higher energy density and lower power density of the primary cell 505 can provide a relatively lower power to the motor 405 over a longer duration, and the lower energy density and higher power density of the secondary cell 510 can provide a relatively higher power to the motor 405 over a shorter duration. The controller 515 may also be configured to selectively couple the primary cell 505 to the secondary cell 510 for a charging period so that the primary cell 505 can charge the secondary cell 510. In some embodiments, the power module 400 may also comprise a switchable load resistor, which can reduce leakage current during storage and autoclave cycles. Additionally, or alternatively, the controller 515 may selectively couple the secondary cell 510 to the resistor to discharge the secondary cell 510. For example, the secondary cell 510 may be discharged before an autoclave cycle. A thermoelectric generator may also be used to charge the primary cell 505, the secondary cell 510, or both during an autoclave cycle.

Figure 6:
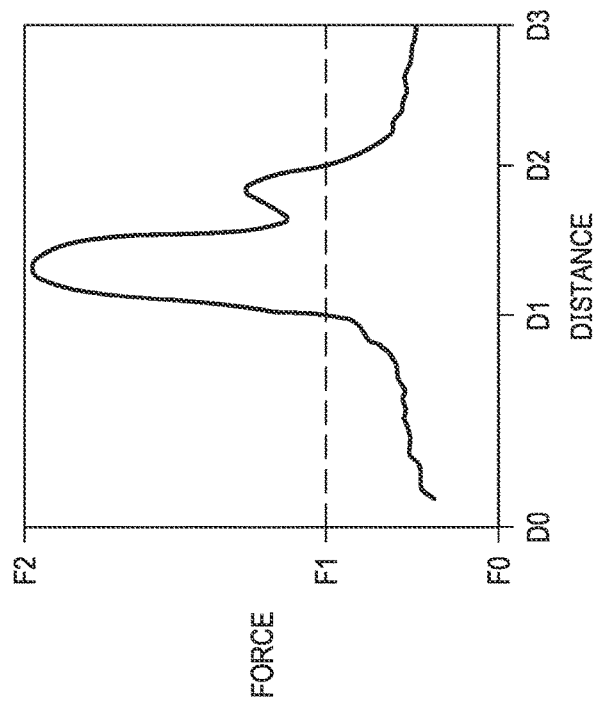
FIG. 6 is a schematic diagram of an example power profile that may be associated with the example power module of FIG. 5.

FIG. 6 is a simplified chart illustrating an example power profile that may be associated with some embodiments of the power module 400 of FIG. 5. More particularly, the chart of FIG. 6 illustrates a force that can be provided by the motor 405 if selectively coupled to the primary cell 505 and the secondary cell 510 over different delivery ranges.

In some embodiments, the delivery ranges may be based on movement of the drive shaft 410. For example, the encoder wheel 425 may provide a signal to the controller 515 that is indicative of a position of the drive shaft 410, such as the distance of the drive shaft 410 from a nominal starting point D0. Additionally, or alternatively, the delivery ranges may be based on energy measurements, such as current measured from the motor 405. For example, a current sensor (not shown) may provide a signal to the controller 515 that is indicative of power requirements from the motor 405, and the controller 515 may switch between the primary cell 505 and the secondary cell 510 over different delivery ranges based on this signal. In the example of FIG. 6, the controller 515 couples the primary cell 505 to the motor 405 for a first delivery range of D0 to D1, and the motor 405 can provide a delivery force to the drive shaft 410 in a first force range of F0 to F1. In a second delivery range of D1 to D2, the controller 515 may switch the motor 405 to the secondary cell 510, and the motor 405 can provide a delivery force to the drive shaft 410 in a second force range of F1 to F2. In a third delivery range of D2 to D3, the controller 515 may switch the motor 405 back to the primary cell 505, and the motor 405 can provide a delivery force in the first force range of F0 to F1. In the example of FIG. 6, the second delivery range of D1 to D2 is shorter than the first delivery range of D0 to D1, and the first force range of F0 to F1 is less than the second force range of F1 to F2.

Figure 7A:
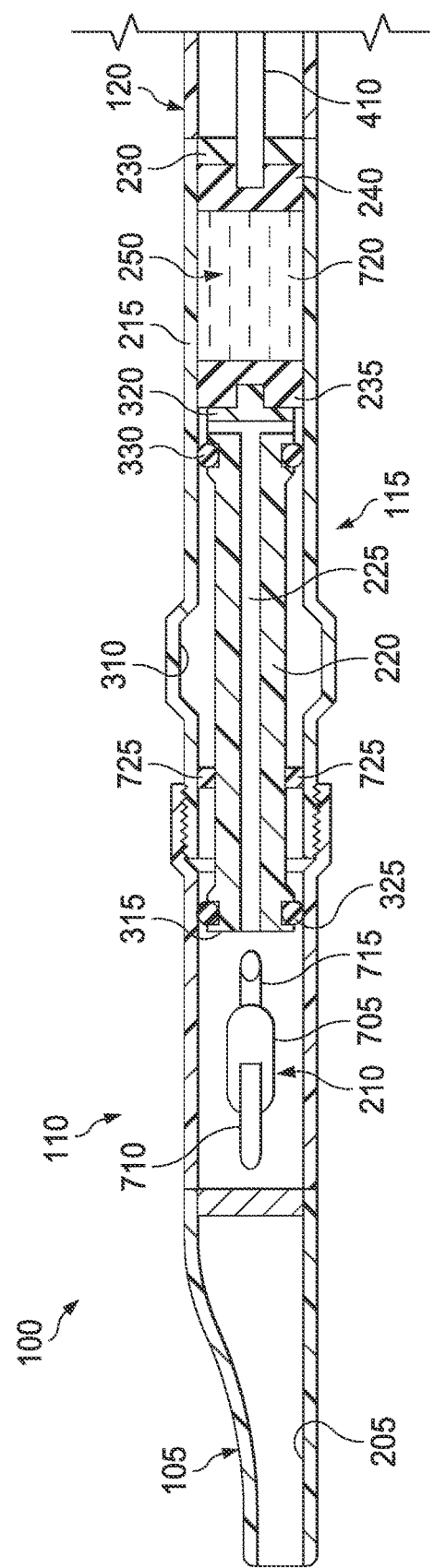
FIGS. 7A-7C are schematic diagrams illustrating an example method of ejecting an implant from the system of FIG. 1.
Figure 7B:
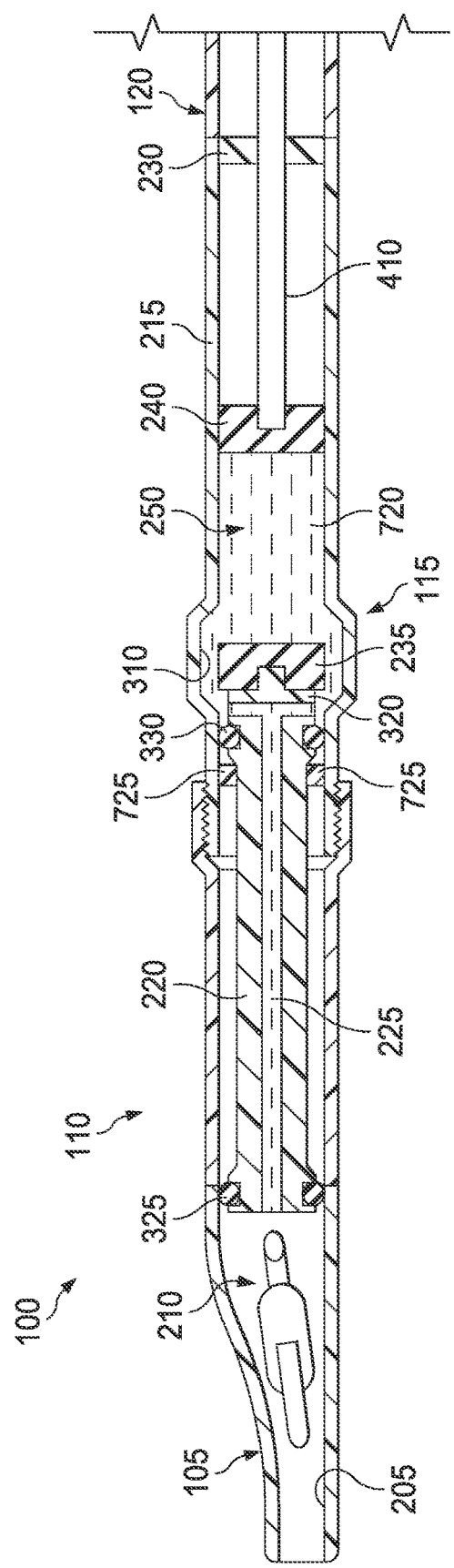
Figure 7C:
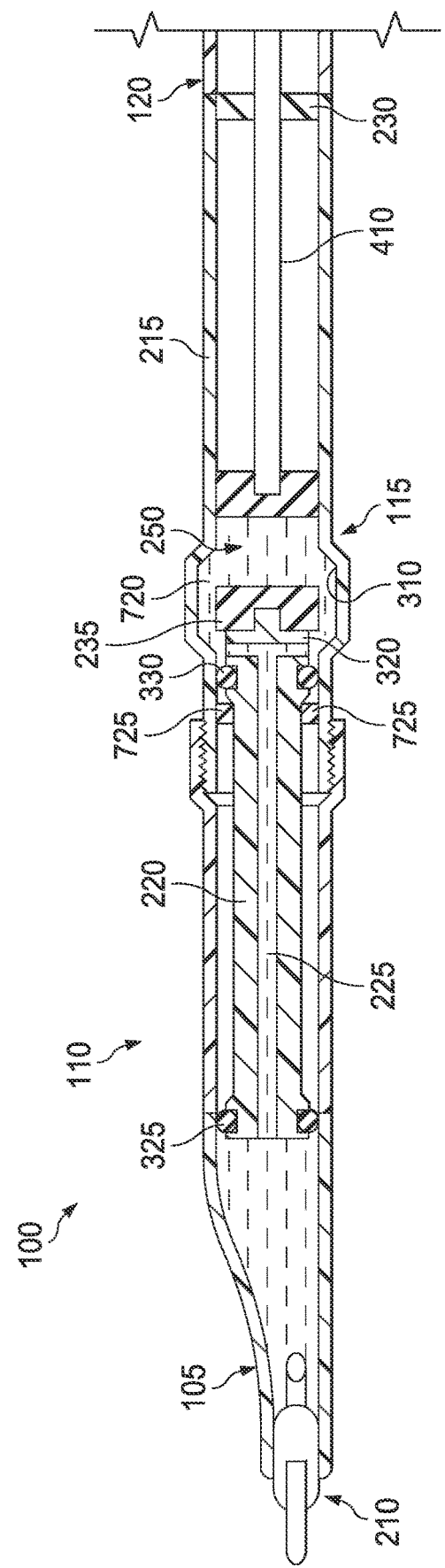

FIGS. 7A-7C are schematic diagrams illustrating an example method of ejecting the implant 210 from the system 100. Initially, various components of the system 100 may be assembled if needed. For example, the nozzle 105, the implant bay 110, and the actuator 115 may be coupled to each other as illustrated in FIG. 7A. The drive module 120 may also be coupled to the actuator 115 through the drive interface 230. For example, the drive shaft 410 may be configured to directly engage the drive seal 240 through the drive interface 230, as illustrated in FIG. 7A. In other examples, the actuator interface 415 may be configured to engage the drive seal 240 through the drive interface 230. In some embodiments, the drive interface 230 may comprise an aperture configured to receive the drive shaft 410, the actuator interface 415, or both.

The implant 210 may be provided in the implant bay 110, as illustrated in the example of FIG. 7A. In some embodiments, the implant 210 may comprise an intraocular lens, which may have a shape similar to that of a natural lens of an eye, and it may be made from numerous materials. In the example of FIG. 7A, the implant 210 is illustrative of an intraocular lens having an optic body 705, a leading haptic 710, and a trailing haptic 715. Examples of suitable materials may include silicone, acrylic, and combinations of such suitable materials. In some instances, the implant 210 may comprise an intraocular lens that is fluid-filled, such as a fluid-filled accommodating intraocular lens.

The plunger 220, the plunger seal 235, and the drive seal 240 are generally movable within the housing between a first position, as illustrated in the example of FIG. 7A, and other positions illustrated in FIG. 7B-7C.

In some examples, a working fluid 720 may be stored in the fluid chamber 250. In the first position of FIG. 7A, the plunger seal 235 fluidly isolates the bore 225 from the working fluid 720 in the fluid chamber 250, which can allow the working fluid 720 to be stored within the fluid chamber 250 in the first position. In some examples, the nozzle seal 325 and the first end 315 of the plunger 220 may protrude into the implant bay 110 in the first position, as illustrated in FIG. 7A, which can create a seal in the implant bay 110 behind the implant 210. The first end 315 of the plunger 220 may also engage the implant 210 in the first position, in some examples. In other examples, the nozzle seal 325 and the first end 315 may be contained within the housing 215 in the first position.

In some embodiments, the drive module 120 may move the drive shaft 410 against the drive seal 240, which can rigidly move the plunger 220, the plunger seal 235, the drive seal 240, and the working fluid 720, maintaining a fixed relationship as illustrated in FIG. 7B. For example, the controller 515 may engage the motor 405 to the primary cell 505 to provide a delivery force in the first range of F0 to F1 to the drive shaft 410, and the delivery force of the drive shaft 410 can move the plunger 220, the plunger seal 235, the drive seal 240, and the working fluid 720 from the first position of FIG. 7A to the second position of FIG. 7B. In some embodiments, the movement from the first position to the second position may correlate to moving the drive shaft 410 through the first delivery range of D0 to D1 in FIG. 6.

In the position of FIG. 7B, the implant 210 is advanced into the delivery lumen 205, which may create a fluid seal between the implant 210 and the delivery lumen 205. In some examples, the implant 210 may be positioned entirely within the delivery lumen 205. In the second position, the bypass channel 310 fluidly couples the bore 225 to the fluid chamber 250 around the plunger seal 235. As the drive shaft 410 and the drive seal 240 apply pressure to the working fluid 720 in the fluid chamber 250, the working fluid 720 may move into the bore 225 through the bypass channel 310, unimpeded at a higher flow rate.

The plunger 220 may be retained in the second position of FIG. 7B against further force applied to the drive seal 240. For example, in some embodiments, the second end 320 of the plunger 220 may be flared, and the plunger interface 305 may be configured to engage the second end 320 to limit advancement. Additionally, or alternatively, the implant bay 110 or the nozzle 105 may comprise a plunger stop 725 configured to engage some portion or feature of the plunger 220, such as the second end 320 of the plunger 220, to prevent further advancement. In yet other examples, some embodiments of the delivery lumen 205 may be tapered, which can prevent further advancement of the plunger 220 into the delivery lumen 205. For example, the diameter of the delivery lumen 205 may decrease as it gets further from the implant bay 110.

With the plunger 220 retained, additional pressure applied by the drive seal 240 on the working fluid 720 can move the working fluid 720 through the bypass channel 310 and the bore 225, as illustrated in the example of FIG. 7C. Movement of the working fluid 720 from the bore 225 into the delivery lumen 205 under pressure from the drive seal 240 can increase the pressure and flow rate of the working fluid 720 in the delivery lumen 205 behind the implant 210, which can advance the implant 210 further through the delivery lumen 205 until the implant 210 is ejected. In some embodiments, additional force from the drive shaft 410 may be advantageous for moving the working fluid 720 through the bore 225 and the delivery lumen 205 behind the implant 210 and moving the implant 210 through the delivery lumen 205. To provide additional force, the controller 515 may switch the motor 405 to the secondary cell 510 to increase the power density available to the motor 405. For example, the secondary cell 510 may provide a higher power density than the primary cell 505, which can be used to provide a delivery force in the second range of F1 to F2 to drive the drive shaft 410 from the second position of FIG. 7B to the third position of FIG. 7C, which may correlate to the second delivery range of D1 to D2 in FIG. 6.

Figure 8A:
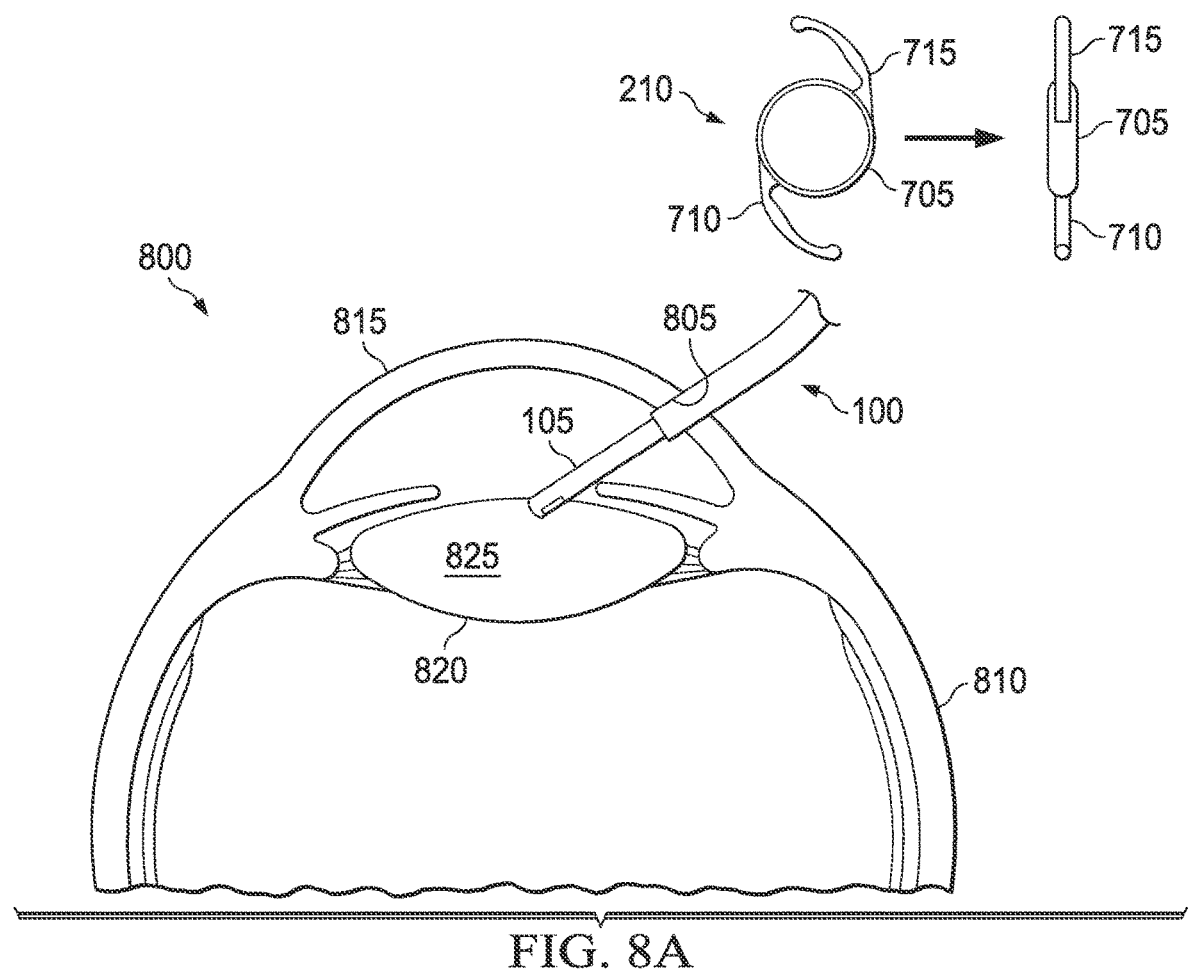
FIG. 8A-8B are schematic diagrams illustrating an example application of the system of FIG. 1 to insert an implant into an eye.
Figure 8B:
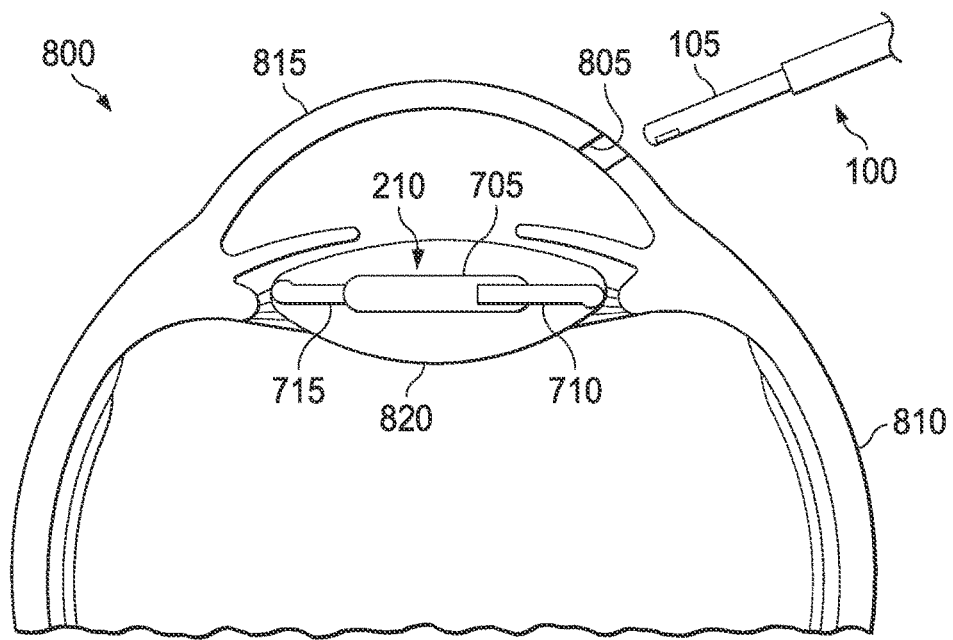

FIGS. 8A-8B are schematic diagrams further illustrating an example use of the system 100 to deliver the implant 210 to an eye 800. As illustrated, an incision 805 may be made in the eye 800 by a surgeon, for example. In some instances, the incision 805 may be made through the sclera 810 of the eye 800. In other instances, an incision may be formed in the cornea 815 of the eye 800. The incision 805 may be sized to permit insertion of a portion of the nozzle 105 in order to deliver the implant 210 into the capsular bag 820. For example, in some instances, the size of the incision 805 may have a length less than about 3000 microns (3 millimeters). In other instances, the incision 805 may have a length of from about 1000 microns to about 1500 microns, from about 1500 microns to about 2000 microns, from about 2000 microns to about 2500 microns, or from about 2500 microns to about 3000 microns.

After the incision 805 is made, the nozzle 105 can be inserted through the incision 805 into an interior portion 825 of the eye 800. The system 100 can then eject the implant 210 through the nozzle 105 into the capsular bag 820 of the eye 800, substantially as described above with reference to FIGS. 7A-7C. In some applications, the implant 210 may be delivered with one or more of the leading haptic 710 and the trailing haptic 715 in a folded configuration and can revert to an initial, unfolded state, within the capsular bag 820, as shown in FIG. 8B. The capsular bag 820 can retain the implant 210 within the eye 800 in a relationship relative to the eye 800 so that the optic body 705 refracts light directed to the retina (not shown). The leading haptic 710 and the trailing haptic 715 can engage the capsular bag 820 to secure the implant 210 therein. After dispensing the implant 210 into the capsular bag 820, the nozzle 105 may be removed from the eye 800 through the incision 805, and the eye 800 can be allowed to heal over a period of time.

The systems, apparatuses, and methods described herein may provide significant advantages. For example, some embodiments may be particularly advantageous for delivering intraocular lenses, including fluid-filled accommodating lenses, which can present unique challenges for delivery.

Some embodiments can compress a relatively large lens to fit through an acceptably small incision, manage deformation caused by shifting fluid during compression and exit from a nozzle, and execute delivery in a predictable and controlled manner. Additionally, some embodiments can reduce system complexity and the number of delivery steps while maintaining haptic position consistency. Some embodiments may also reduce the amount of working fluid for delivery.

Additionally, or alternatively, some embodiments may provide a hybrid power delivery, which may be advantageous for delivering some implants. For example, some embodiments of the power module 400 may provide both a relatively lower power over a longer distance and a relatively higher peak power over a shorter distance. In some embodiments of the system 100, the implant 210 may be larger than the delivery lumen 205 and may benefit from the hybrid power profile provided by some embodiments of the power module 400 that can provide lower power to move the implant 210 into the delivery lumen 205 and increased power to move the implant 210 through the delivery lumen 205. Hybrid power may also support long-term, low-level energy requirements, which may be advantageous for some embodiments. More particular advantages may include reducing the cost and complexity of batteries and other power cells.

Actuation force experienced by an operator may also be reduced in some embodiments. For example, a surgeon may only feel the actuation force of the switch, which can be significantly lower than some types of mechanical drive systems. Additionally, or alternatively, some embodiments may include facilitating one-handed operation and reversal, which can also reduce the number of staff required to perform a surgical procedure.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations, the nozzle 105, the implant bay 110, the actuator 115, the drive module 120 may each be separated from one another or combined in various ways for manufacture or sale.

The claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. An apparatus for operating an implant delivery device, the apparatus comprising:
   a motor;
   a drive shaft coupled to the motor and configured to be coupled to the implant delivery device, the drive shaft having a first delivery range and a second delivery range;
   a primary cell having a first energy density and a first power density;
   a secondary cell having a second energy density and a second power density; and
   a controller coupled to the motor, the primary cell, and the secondary cell; the controller configured to:
   receive a signal indicative of a position of the drive shaft; and
   based on the signal indicating the position is in the second delivery range, perform at least both of:
   (i) disconnecting the primary cell from the motor, and
   (ii) coupling the secondary cell to the motor.

2. The apparatus of claim 1, wherein the second power density is greater than the first power density.

3. The apparatus of claim 1, wherein the first energy density is greater than the second energy density.

4. The apparatus of claim 1, wherein the first delivery range is greater than the second delivery range.

5. The apparatus of claim 4, wherein the controller is further configured to couple the primary cell to the motor if the position is in the first delivery range.

6. The apparatus of claim 1, wherein at least one of the primary cell and the secondary cell is a battery.

7. The apparatus of claim 1, wherein the secondary cell is a capacitor.

8. The apparatus of claim 1, wherein the secondary cell is a supercapacitor.

9. The apparatus of claim 1, wherein the controller is further configured to selectively couple the primary cell to the secondary cell for a charging period.

10. The apparatus of claim 1, wherein the controller is further configured to discharge the secondary cell.

11. The apparatus of claim 1, further comprising a thermoelectric generator configured to charge at least one of the primary cell and the secondary cell.

12. The apparatus of claim 1, wherein the controller is further configured to couple the primary cell to the motor if the position is in the first delivery range.

13. The apparatus of claim 1, wherein the controller is configured to couple the primary cell to the motor based on the signal indicating the position is in the first delivery range.

* * * * *